(12) United States Patent
Ali et al.

(10) Patent No.: US 8,106,034 B2
(45) Date of Patent: Jan. 31, 2012

(54) ANGIOTENSIN II RECEPTOR ANTAGONISTS

(75) Inventors: Amjad Ali, Freehold, NJ (US); Michael Man-Chu Lo, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/864,448

(22) PCT Filed: Jan. 29, 2009

(86) PCT No.: PCT/US2009/032323
§ 371 (c)(1),
(2), (4) Date: Jul. 23, 2010

(87) PCT Pub. No.: WO2009/099853
PCT Pub. Date: Aug. 13, 2009

(65) Prior Publication Data
US 2010/0298277 A1    Nov. 25, 2010

Related U.S. Application Data

(60) Provisional application No. 61/065,082, filed on Feb. 8, 2008.

(51) Int. Cl.
*A61K 31/655* (2006.01)
*C07C 291/08* (2006.01)
*A61P 9/12* (2006.01)

(52) U.S. Cl. ........................................ 514/149; 534/551

(58) Field of Classification Search .................. None
See application file for complete search history.

(56) References Cited

U.S. PATENT DOCUMENTS
2007/0032533 A1    2/2007    Garvey et al.

FOREIGN PATENT DOCUMENTS
WO    WO2005/011646        2/2005
WO    WO2006/000294 A1    1/2006
WO    WO2007/144512 A2    12/2007

OTHER PUBLICATIONS

Cordi et al., caplus an 2007:1449159.*
Cordi et al., caplus and 2007:1449159.*
AngiotensinIIReceptorAntagonist, 2011, http://en.wikipedia.org/wiki/Angiotensin_ll_receptor_antagonist.*
PCT International Search Report performed by ISA/US; Mailing Date: May 13, 2009; by authorized officer Lee W. Young.

* cited by examiner

*Primary Examiner* — Sun Jae Loewe
(74) *Attorney, Agent, or Firm* — Richard S. Parr; Mark R. Daniel; Catherine D. Fitch

(57) ABSTRACT

A compound having the structure $$R-Y$$
$$|$$
$$[Y]_{0-1}$$

wherein R is an angiotensin receptor blocking group
Y is $-(CR^1R^{20})_{1-7}R^5$, or $-C(O)(CR^1R^{20})_{1-7}R^5$;
$R^1$ and $R^{20}$ are independently selected from the group consisting of hydrogen or $C_{1-4}$ alkyl;
$R^5$ is $-O-N=N(O)-NR^3R^4$; and
$R^3$ and $R^4$ are independently selected from the group consisting of $-CH_2CH_2OH$, $-CH_2CH_2OCH_3$, $-C_{1-4}$ alkyl, unsubstituted or substituted $C_{1-6}$ alkenyl, unsubstituted or substituted morpholino, amino, unsubstituted or substituted benzyl, unsubstituted or substituted phenyl, unsubstituted or substituted aryl$C_{1-4}$ alkyl,
or $R^3$ and $R^4$ together with the nitrogen atom to which they are attached, form a ring selected from the group consisting of or a stereoisomer thereof, or a pharmaceutically acceptable salt thereof, or a pharmaceutically acceptable salt of the stereoisomer thereof, which is useful for treating hypertension.

11 Claims, No Drawings

ANGIOTENSIN II RECEPTOR ANTAGONISTS

CROSS REFERENCE TO RELATED APPLICATIONS

This application is a U.S. National Phase application under 35 U.S.C. §371 of PCT Application No. PCT/US2009/032323 filed Jan. 29, 2009, which claims priority under 35 U.S.C. §119(e) from U.S. Provisional Application No. 61/065,082 filed on Feb. 8, 2008.

BACKGROUND OF THE INVENTION

U.S. Pat. No. 5,138,069 generically and specifically describes 2-butyl-4-chloro-1-[p-(o-1H-tetrazol-5-ylphenyl)-benzyl]imidazole-5-methanol potassium salt and 2-butyl-4-chloro-1-[(2'-1H-tetrazol-5-yl)biphenyl-4-yl)methyl]imidazole-5-carboxylic acid. Columns 261-263 of U.S. Pat. No. 5,136,069 describe general procedures for formulating compounds described in the patent, including capsules, tablets, injection formulations, and suspensions. U.S. Pat. No. 5,153,197, describes the use of these compounds, alone and in combination with a diuretic, to treat a patient having hypertension.

SUMMARY OF THE INVENTION

The present invention includes angiotensin II receptor antagonist diazeniumdiolate derivatives, including various pharmaceutically acceptable salts and hydrates of these forms, and pharmaceutical formulations for controlled and sustained delivery of these forms to a patient.

The salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention also includes a method for treating hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, by administering an angiotensin II receptor antagonist of the invention to a patient having one or more of these conditions.

DETAILED DESCRIPTION OF THE INVENTION AND PREFERRED EMBODIMENTS

Compounds of the invention are angiotensin II receptor antagonist diazeniumdiolate derivatives having the general formula:

$$R-Y$$
$$|$$
$$[Y]_{0-1}$$

wherein R is selected from the group consisting of

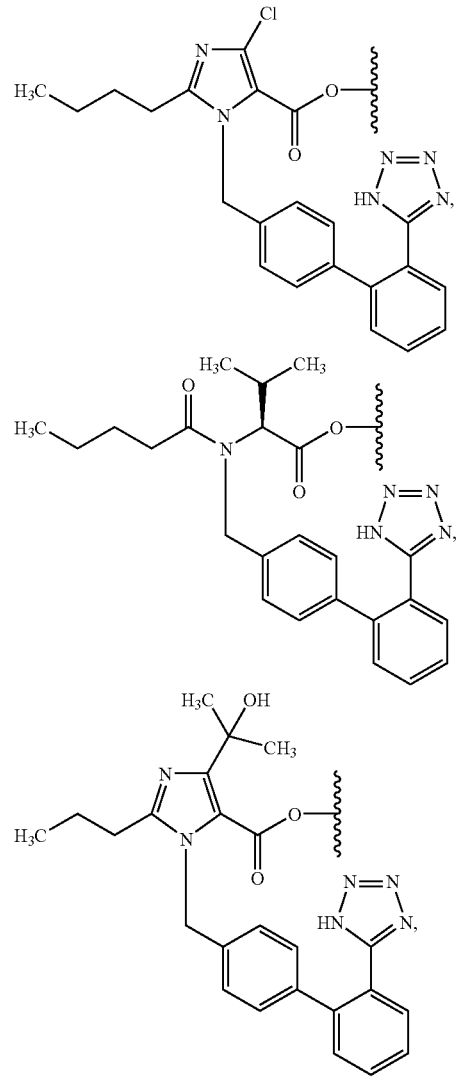

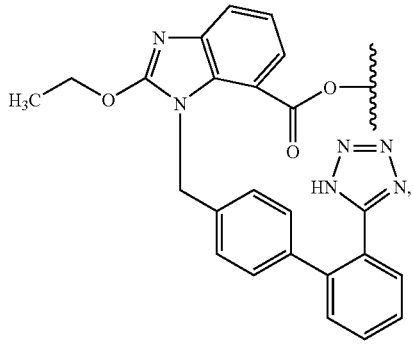
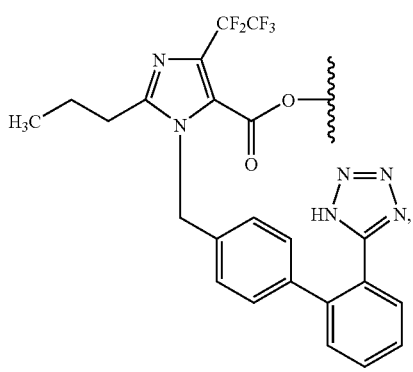
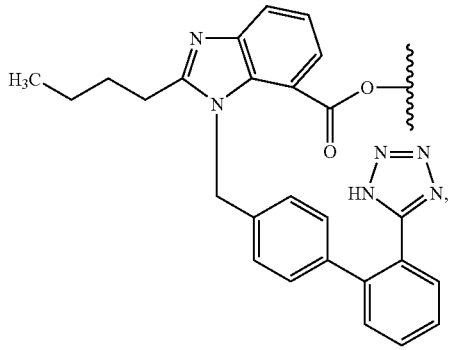
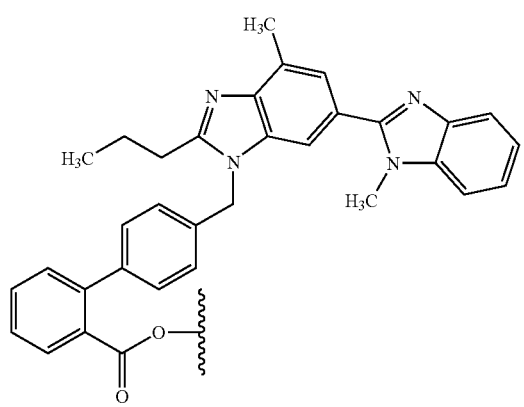

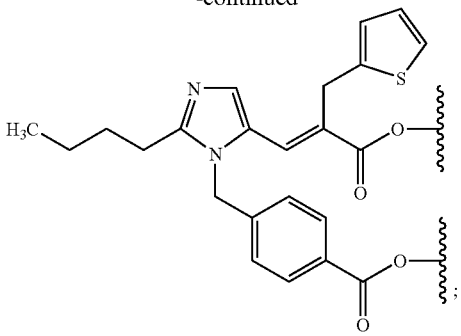

Y is —(CR$^1$R$^{20}$)$_{1-7}$R$^5$, or —C(O)(CR$^1$R$^{20}$)$_{1-7}$R$^5$;

R$^1$ and R$^{20}$ are independently selected from the group consisting of hydrogen or C$_{1-4}$ alkyl;

R$^5$ is —O—N=N(O)—NR$^3$R$^4$;

R$^3$ and R$^4$ are independently selected from the group consisting of —CH$_2$CH$_2$OH, —CH$_2$CH$_2$OCH$_3$, —C$_{1-4}$ alkyl, unsubstituted or substituted C$_{1-6}$ alkenyl, unsubstituted or substituted morpholino, amino, unsubstituted or substituted benzyl, unsubstituted or substituted phenyl, unsubstituted or substituted arylC$_{1-4}$ alkyl, or R$^3$ and R$^4$ together with the nitrogen atom to which they are attached, form a ring selected from the group consisting of

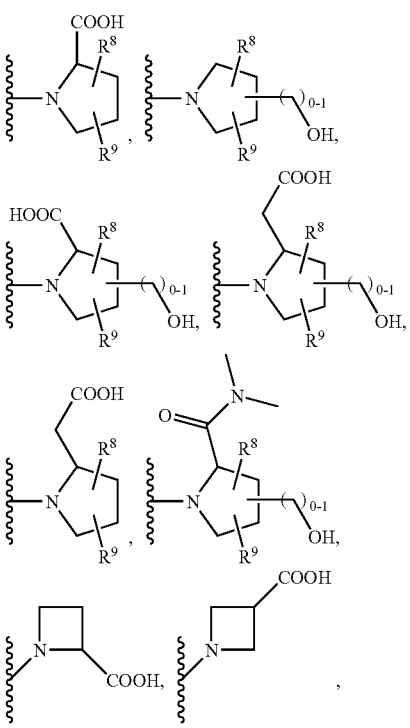
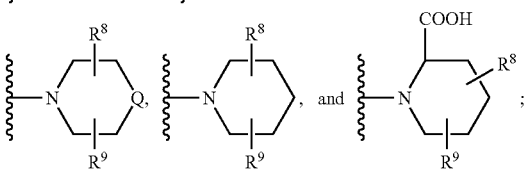

Q is selected from the group consisting of S, O and $NR^6$;
$R^6$, $R^8$ and $R^9$ are independently selected from the group consisting of hydrogen and unsubstituted or substituted $C_{1-6}$ alkyl;
$R^{12}$ and $R^{13}$ are independently selected from the group consisting of —OH, —$CH_2OH$, —$CH_2CH_2OH$, —COOH, and —$CH_2COOH$;
W is straight or branched $C_{1-10}$ alkylene;
n is an integer from 1 to 8;
Y is selected from the group consisting of
—$(CH_2)_{1-4}$—$(CH_2)_{0-4}$,
—$(CH_2)_{1-4}$—O—$(CH_2)_{0-4}$,
—$(CH_2)_{1-4}$—$CR^{10}R^{11}$—$(CH_2)_{0-4}$,
$R^{10}$ and $R^{11}$ are independently selected from the group consisting of hydrogen and $C_{1-4}$ alkyl;
$R^2$ is selected from the group consisting of —$CH_3$, —$CH_2CH_3$, and —$CH(CH_3)_2$;
or a pharmaceutically acceptable salt thereof.

In one embodiment, compounds of the invention are angiotensin II receptor antagonist diazeniumdiolate derivatives having the general formula:

R—Y
|
[Y]$_{0-1}$ wherein R is selected from the group consisting of

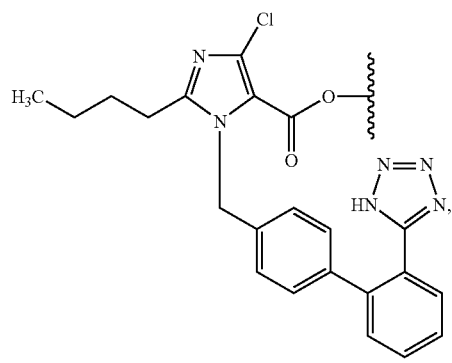

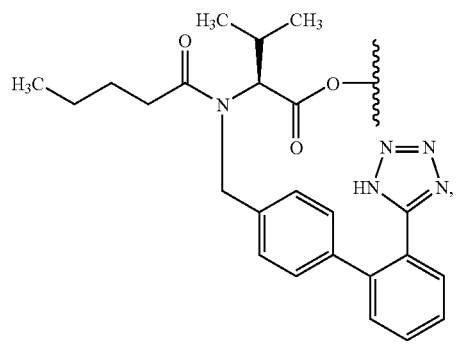

-continued

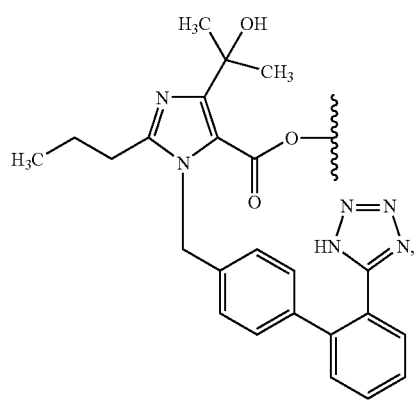

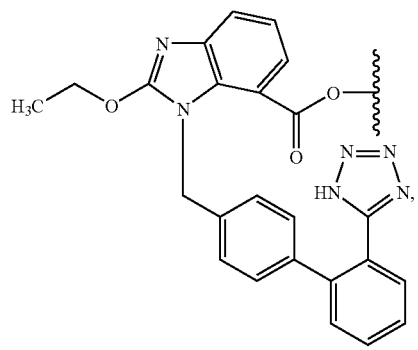

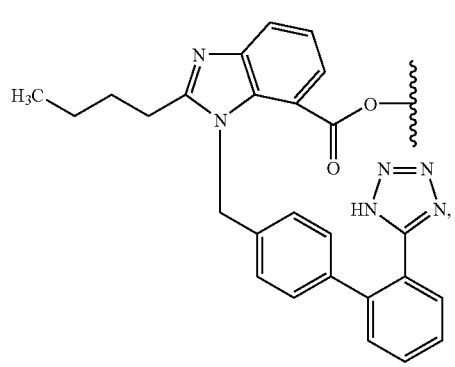

-continued

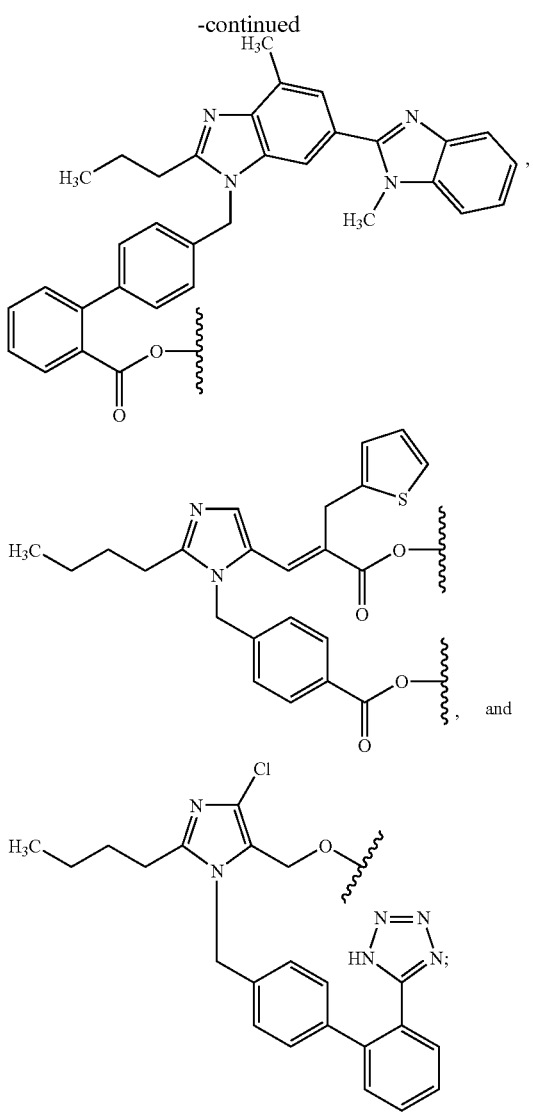

Y is —CHR$^1$(CH$_2$)$_{0-2}$R$^5$, or —C(O)CHR$^1$(CH$_2$)$_{0-2}$R$^5$, provided that when Y is
—C(O)CHR$^1$(CH$_2$)$_{0-2}$R$^5$, R is

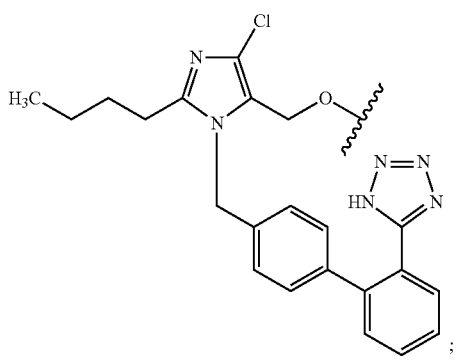

R$^1$ is hydrogen or C$_{1-4}$ alkyl;
R$^5$ is —O—N=N(O)—NR$^3$R$^4$;
R$^3$ and R$^4$ are independently selected from the group consisting of unsubstituted or substituted C$_{1-6}$ alkenyl, unsubstituted or substituted morpholino, amino, unsubstituted or substituted benzyl, unsubstituted or substituted phenyl, unsubstituted or substituted arylC$_{1-4}$ alkyl, or R$^3$ and R$^4$ together with the nitrogen atom to which they are attached, form a ring selected from the group consisting of

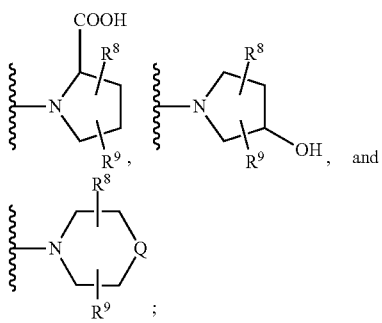

Q is selected from the group consisting of S, O and NR$^6$;
R$^6$, R$^8$ and R$^9$ are independently selected from the group consisting of hydrogen and unsubstituted or substituted C$_{1-6}$ alkyl;
or a pharmaceutically acceptable salt thereof.

In another embodiment, R$^1$ is H or CH$_3$ and all other variables are as previously defined.

In another embodiment, R$^3$ and R$^4$ together with the nitrogen atom to which they are attached, form a ring selected from the group consisting of

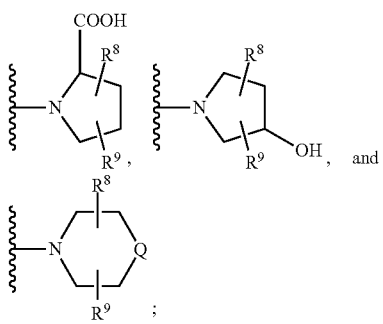

and all other variables are as previously defined.

In another embodiment, R$^3$ and R$^4$ together with the nitrogen atom to which they are attached, form a ring selected from the group consisting of

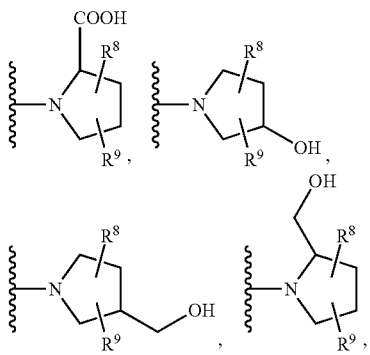

-continued

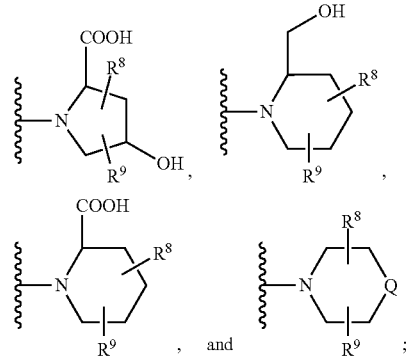

and all other variables are as previously defined.

In another embodiment, $R^8$ and $R^9$ are hydrogen.

In another embodiment. R is selected from the group consisting of

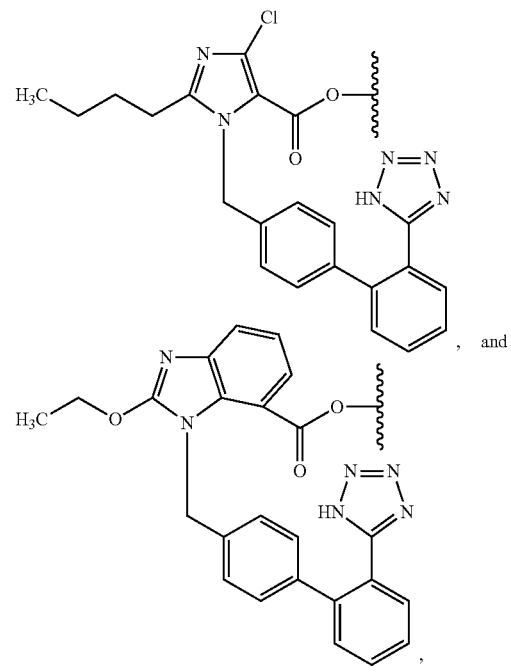

and all other variables are as previously defined.

In another embodiment the compound is selected from the group consisting of

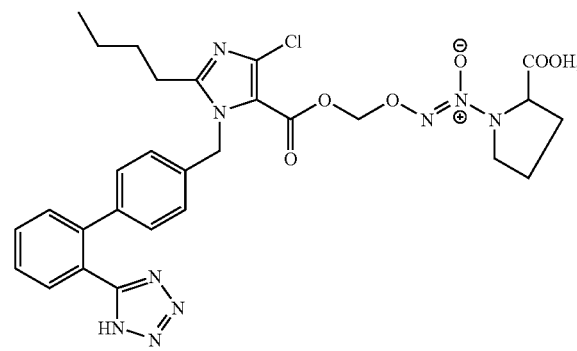

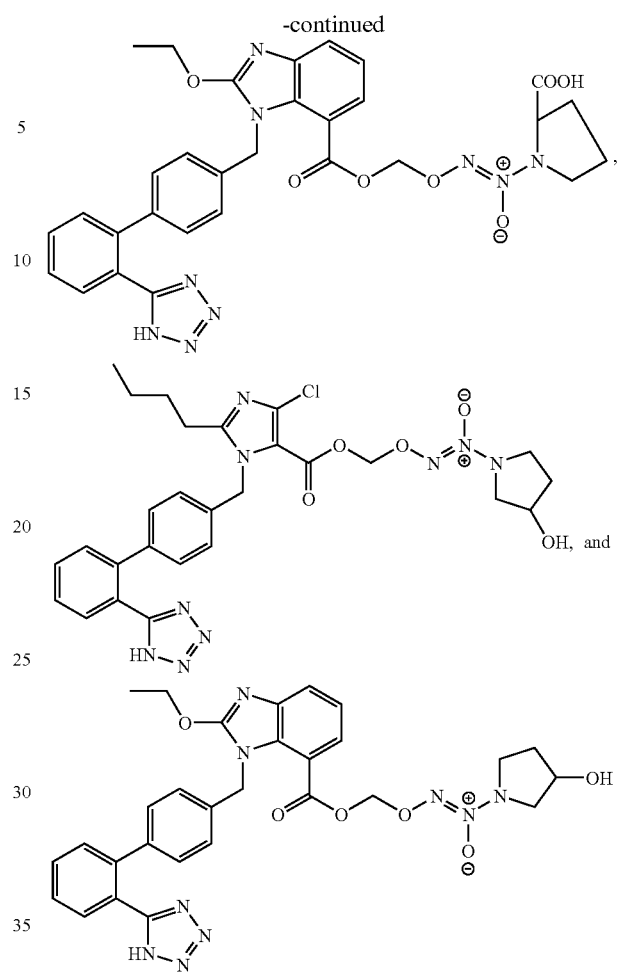

In another embodiment, the compound is selected from the group consisting of

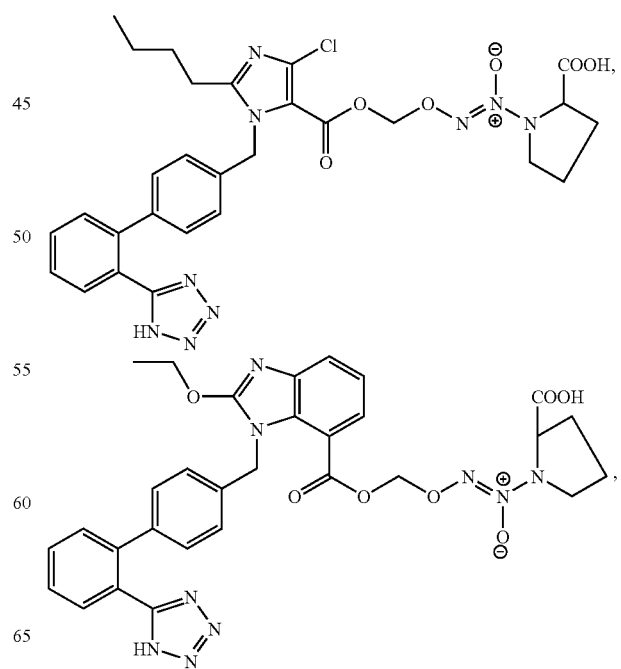

11
-continued
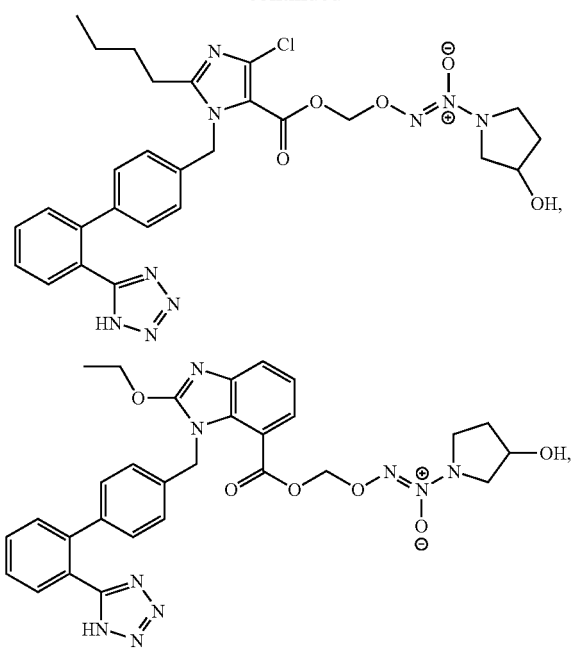
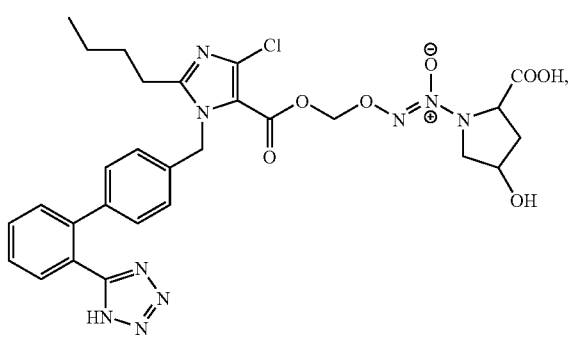
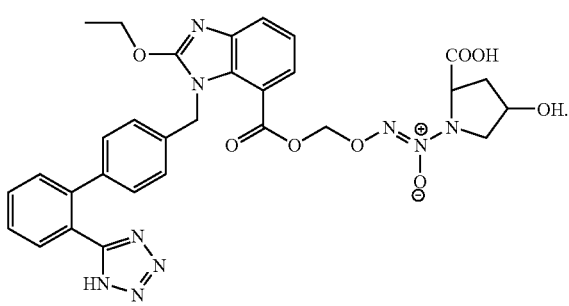
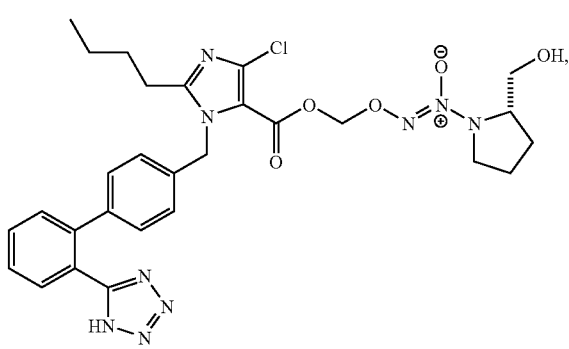
12
-continued
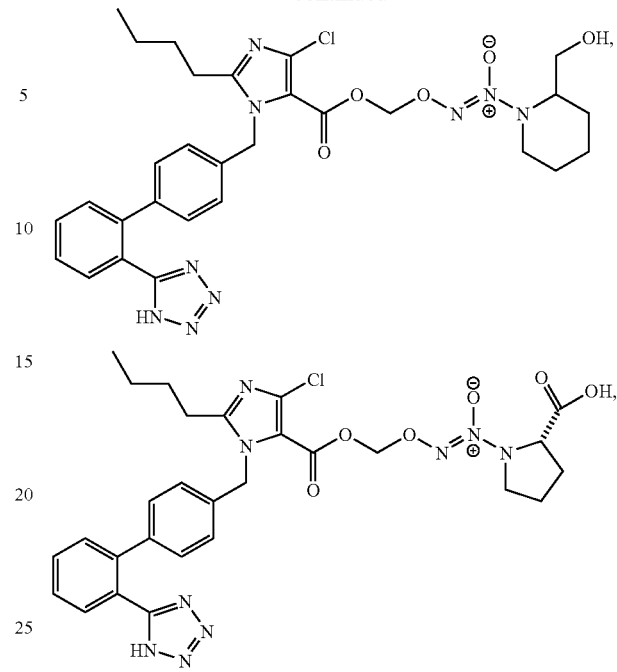
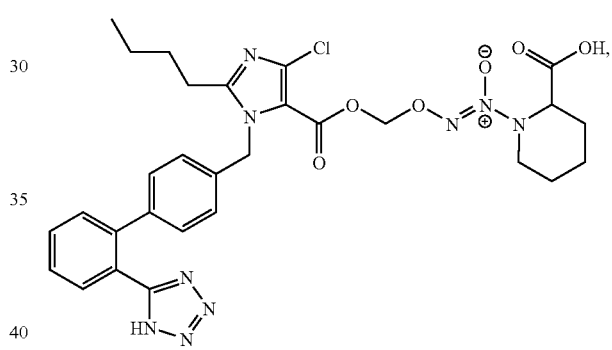
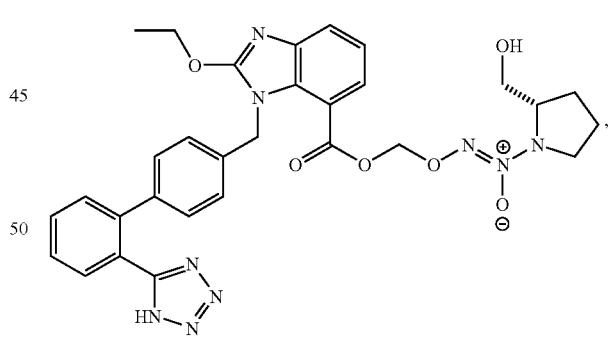
, and -continued

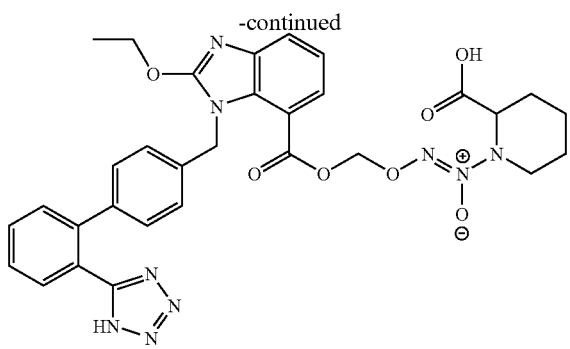

The compounds of the present invention may have one or two chiral centers, providing for up to two ((R) and (S)) or four (R,R), (S,S), (R,S), and (S,R) stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. The structure marking "*" indicates the location of a carbon atom that is a chiral center.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups. The term "alkenyl" includes both branched and straight chain unsaturated hydrocarbon groups containing at least two carbon atoms joined by a double bond. The alkene ethylene is represented, for example, by "$CH_2CH_2$" or alternatively, by "$H_2C=CH_2$". "$C_{2-5}$ alkenyl" (or "$C_2$-$C_5$ alkenyl") for example, means linear or branched chain alkenyl groups having from 2 to 5 carbon atoms and includes all of the pentenyl isomers as well as 1-butenyl, 2-butenyl, 3-butenyl, 1-propenyl, 2-propenyl, and ethenyl (or ethylenyl). Similar terms such as "$C_{2-3}$ alkenyl" have an analogous meaning. The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings. The term "aryl" refers to a functional group or substituent derived from a simple aromatic ring, e.g., phenyl, benzyl, tolyl, o-xylyl. The term "benzyl" refers to —$CH_2C_6H_5$. The term "phenyl" refers to —$C_6H_5$. The term "amino" refers to $NH_2$. The term "morpholino" refers to the ring

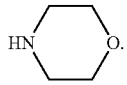

Unless otherwise specifically noted as only "unsubstituted" or only "substituted", morpholino, benzyl, phenyl, aryl, alkyl, alkenyl, and cycloalkyl groups are unsubstituted or substituted, where substituted groups may contain from 1 to 3 substituents in addition to the point of attachment to the rest of the compound, wherein such substituents result in formation of a stable compound. Preferably, the substituents are selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) $S(O)_{0-2}$—, aryl-$S(O)_{0-2}$—, ($C_0$-$C_6$ alkyl)$S(O)_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, haloaryl, halo-aralkyl, halo-heterocycle, halo-heterocyclylalkyl, cyano-aryl, cyano-aralkyl, cyano-heterocycle and cyano-heterocyclylalkyl.

The angiotensin II receptor antagonists of the invention are useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system.

The angiotensin II receptor antagonists of the invention are especially useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In one embodiment, the invention relates to a method for the treatment and/or prophylaxis of diseases, which are associated with a dysregulation of the renin-angiotensin system, in particular to a method for the treatment or prophylaxis of the above-mentioned diseases, said methods comprising administering to a patient a pharmaceutically active amount of an angiotensin II receptor antagonist of the invention.

The invention also relates to the use of angiotensin II receptor antagonists of the invention for the preparation of a medicament for the treatment and/or prophylaxis of the above-mentioned diseases.

The above-mentioned angiotensin II receptor antagonists of the invention are also of use in combination with other pharmacologically active compounds comprising angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren((2S,4S,5S,7S)-N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone)) or with other drugs beneficial for the prevention or the treatment of the above-mentioned diseases including nitroprusside and diazoxide.

The dosage regimen utilizing the angiotensin II receptor antagonists is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the angiotensin II receptor antagonists, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, and more preferably 25 mg/day to 150 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the angiotensin II receptor antagonists may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The angiotensin II receptor antagonists of the invention can be administered in such oral forms as tablets, capsules and granules. The angiotensin II receptor antagonists are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose aetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

2-Butyl-4-chloro-1-[(2'-(1-H-tetrazol-5-yl)biphenyl-4-yl)methyl]-imidazole-5-carboxylic acid ("E3174") is the active metabolite of 2-butyl-4-chloro-[p-(o-1H-tetrazol-5-ylphenyl)-benzyl]imidazole-5-methanol which is available as a monopotassium salt (also known as losartan potassium salt). Losartan potassium salt is available commercially as the active ingredient in COZAAR® (Merck & Co., Inc. (Whitehouse Station, N.J.)). The preparation of losartan potassium salt is described in U.S. Pat. Nos. 5,138,069, 5,130,439, and 5,310,928. Tetrazolylphenylboronic acid intermediates useful in the synthesis of losartan potassium salt are described in U.S. Pat. No. 5,206,374. Additional patents which describe procedures useful for making losartan include U.S. Pat. Nos. 4,820,843, 4,870,186, 4,874,867, 5,039,814, and 5,859,258.

Compound Preparation

Schemes 1, 2 and 3 describe general procedures for making compounds of the invention in good overall yield. Detailed examples are shown after the schemes.

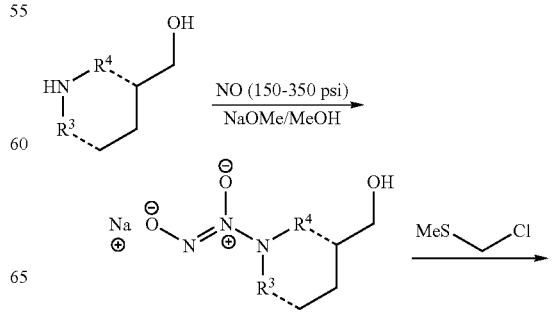

Scheme 1

-continued

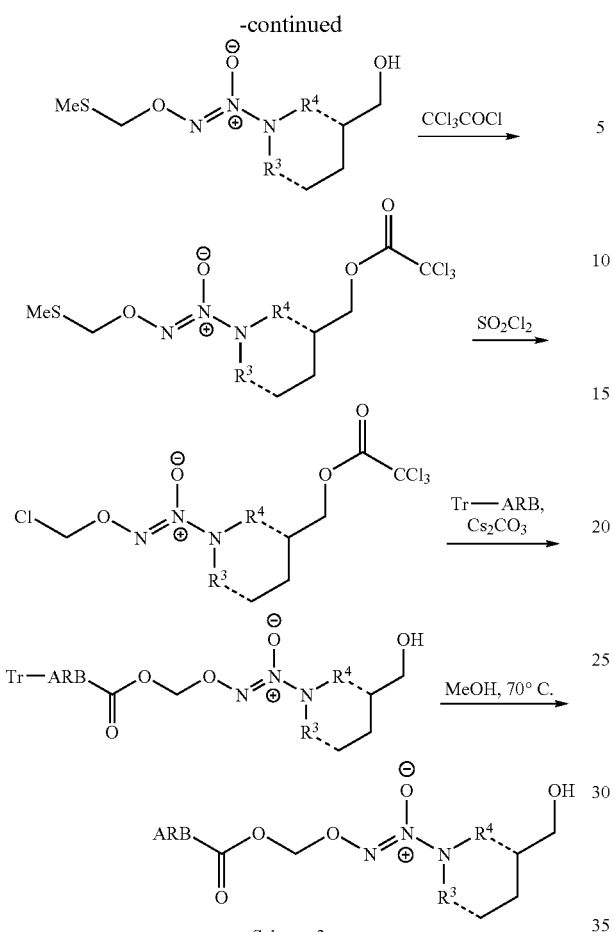

Scheme 2

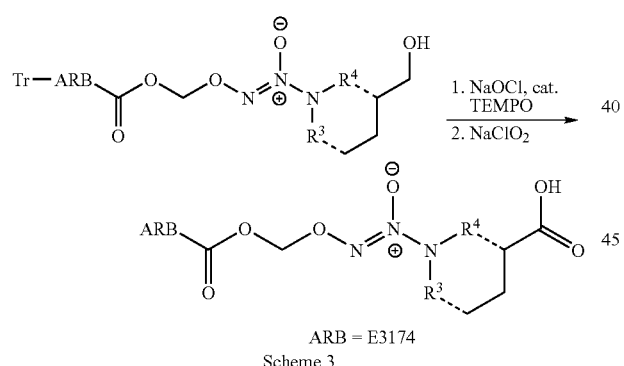

ARB = E3174
Scheme 3

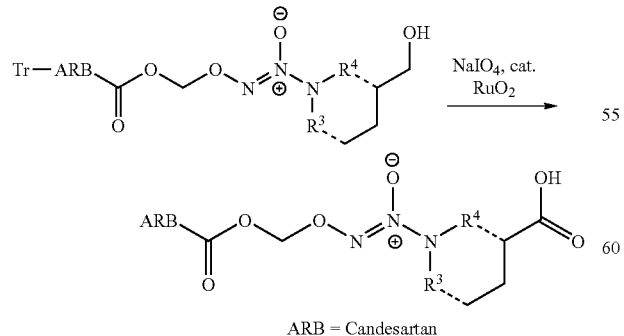

ARB = Candesartan

Tr is a trityl protecting group. $R^3$ and $R^4$ are depicted here where they form a ring as defined above. According to the procedures described above, the following exemplary compounds of the invention can be prepared:

Example 1

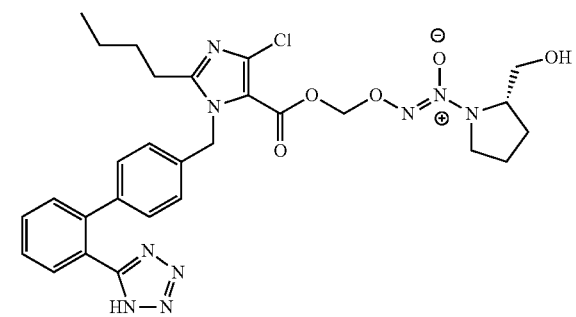

$O^2$-({[(2-butyl-4-chloro-1-{[2'-(1H-tetrazol-5-yl) biphenyl-4-yl]methyl}-1H-imidazol-5-yl)carbonyl] oxy}methyl)1-[2S-(hydroxymethyl)pyrrolidin-1-yl] diazen-1-ium-1,2-diolate Step A: $O^2$-[(methylthio)methyl]1-[2S-(hydroxymethyl)pyrrolidin-1-yl]diazen-1-ium-1,2-diolate To an acetonitrile (40 mL) suspension of sodium 1-[2S-(hydroxymethyl)pyrrolidin-1-yl]diazen-1-ium-1,2-diolate (2.53 g, 13.9 mmol) and potassium carbonate (2.34 g, 16.9 mmol) was added chloromethyl methyl sulfide (1.38 mL, 16.7 mmol). After three days, the reaction mixture was concentrated in vacuo. Chromatography over silica gel, eluting with hexanes/ethyl acetate, afforded the title compound as a yellow oil. $^1$H NMR (500 MHz, CDCl$_3$) δ 1.79-1.85 (m, 1H), 1.93-2.00 (m, 2H), 2.10 (qd, J=8.9, 12.6 Hz, 1H), 2.28 (s, 3H), 2.92 (t, J=5.8 Hz, 1H), 3.57-3.70 (m, 3H), 3.79 (ddd, J=3.8, 5.8, 11.3 Hz, 1H), 4.09-4.15 (m, 1H), 5.25 (s, 2H).

Step B: $O^2$-[(methylthio)methyl]1-{2S-[(trichloroacetoxy)methyl]pyrrolidin-1-yl}diazen-1-ium-1,2-diolate To a dichloromethane (5 mL) solution of $O^2$-[(methylthio) methyl]1-[2S-(hydroxymethyl)pyrrolidin-1-yl]diazen-1-ium-1,2-diolate (120 mg, 0.542 mmol), triethylamine (0.53 mL, 3.8 mmol), 4-dimethylaminopyridine (10 mg, 0.08 mmol) was added trichloroacetyl chloride (0.20 mL, 1.8 mmol). After 18 hours, the reaction mixture was concentrated in vacuo, and the residue was purified by column chromatography on silica, eluting with 7/93→70/30 ethyl acetate/hexanes to give the title compound as a yellow liquid. $^1$H NMR (500 MHz, CDCl$_3$) δ 1.89-2.02 (m, 2H), 2.03-2.21 (m, 2H), 2.28 (s, 3H), 3.58 (dt, J=6.8, 9.9 Hz, 1H), 3.73 (ddd, J=3.0, 6.6, 10.2 Hz, 1H), 4.38-4.44 (m, 1H), 4.50 (dd, J=3.8, 11.1 Hz, 1H), 4.58 (dd, J=5.3, 11.1 Hz, 1H), 5.24 (s, 2H).

Step C: $O^2$-(chloromethyl)1-{2S-[(trichloroacetoxy) methyl]pyrrolidin-1-yl}diazen-1-ium-1,2-diolate To a dichloromethane (10 mL) solution of $O^2$-[(methylthio)methyl]1-{2S-[(trichloroacetoxy)methyl]pyrrolidin-1-yl}diazen-1-ium-1,2-diolate (148 mg, 0.404 mmol) was added 1.0 M dichloromethane solution of sulfuryl chloride (2.8 mL, 2.8 mmol). After 12 hours, the reaction mixture was concentrated in vacuo, and the crude material was brought to the subsequent step without further purification. $^1$H NMR (500 MHz, CDCl$_3$) δ 1.94-2.05 (m, 2H), 2.08-2.21 (m, 2H), 3.62 (dt, J=6.7, 10.0 Hz, 1H), 3.80 (ddd, J=3.1, 6.6, 10.3 Hz, 1H), 4.44-4.51 (m, 2H), 4.61 (dd, J=4.9, 10.9 Hz, 1H), 5.85 (s, 2H).

Step D: O$^2$-({[(2-butyl-4-chloro-1-{[2'-(1-trityl-1H-tetrazol-5-yl)biphenyl-4-yl]methyl}-1H-imidazol-5-yl)carbonyl]oxy}methyl)1-[2S-(hydroxymethyl)pyrrolidin-1-yl]diazen-1-ium-1,2-diolate To a N,N-dimethylformamide (4 mL) solution of 2-butyl-4-chloro-1-{[2'-(1-trityl-1H-tetrazol-5-yl)biphenyl-4-yl]methyl}-1H-imidazole-5-carboxylic acid (1.13 g, 1.66 mmol), cesium carbonate (0.93 g, 2.85 mmol), and tetrabutylammonium hydrogen sulfate (0.236 g, 0.695 mmol) was added a N,N-dimethylformamide (5 mL) solution of O$^2$-(chloromethyl)1-{2S-[(trichloroacetoxy)methyl]pyrrolidin-1-yl}diazen-1-ium-1,2-diolate (0.477 g, 1.34 mmol). After 24 hours, the reaction mixture was charged with water and ethyl acetate, and stirred for 30 minutes. The reaction mixture was diluted with more water and extracted with ethyl acetate. The combined organic extracts were washed with brine, dried (sodium sulfate), and concentrated in vacuo. Chromatography over silica gel, eluting with hexanes/ethyl acetate, afforded the title compound as a pale yellow solid. $^1$H NMR (500 MHz, CDCl$_3$) δ 0.86 (t, J=7.3 Hz, 3H), 1.28 (sextet, J=7.4 Hz, 2H), 1.65 (quintet, J=7.7 Hz, 2H), 1.77-1.82 (m, 1H), 1.88-1.94 (m, 2H), 1.98-2.06 (m, 1H), 2.52 (t, J=7.8 Hz, 2H), 2.67 (t, J=5.8 Hz, 1H), 3.53-3.67 (m, 3H), 3.71-3.77 (m, 1H), 4.07-4.12 (m, 1H), 5.43 (s, 2H), 5.81 (d, J=7.2 Hz, 1H), 5.85 (d, J=7.1 Hz, 1H), 6.78 (d, J=7.9 Hz, 2H), 6.93 (d, J=7.9 Hz, 6H), 7.09 (d, J=7.9 Hz, 2H), 7.26 (t, J=7.6 Hz, 6H), 7.30-7.37 (m, 4H), 7.45 (dt, J=1.6, 7.5 Hz, 1H), 7.49 (dt, J=1.6, 7.4 Hz, 1H), 7.91 (dd, J=1.5, 7.5 Hz, 1H); LC-MS (M+Na) found 874.3.

Step E: O$^2$-({[(2-butyl-4-chloro-1-{[2'-(1H-tetrazol-5-yl)biphenyl-4-yl]methyl}-1H-imidazol-5-yl)carbonyl]oxy}methyl)1-[2S-(hydroxymethyl)pyrrolidin-1-yl]diazen-1-ium-1,2-diolate A methanol (10 mL) solution of O$^2$-({[(2-butyl-4-chloro-1-{[2'-(1-trityl-1H-tetrazol-5-yl)biphenyl-4-yl]methyl}-1H-imidazol-5-yl)carbonyl]oxy}methyl)1-[2S-(hydroxymethyl)pyrrolidin-1-yl]diazen-1-ium-1,2-diolate (141.6 mg, 0.166 mmol) was heated to 70° C. for 2 hours. The reaction mixture was concentrated in vacuo, and the residue was purified by column chromatography, eluting with 5/95→30/70 methanol/dichloromethane to give the title compound as a white solid. $^1$H NMR (500 MHz, CD$_3$CN) δ 0.85 (t, J=7.4 Hz, 3H), 1.31 (sextet, J=7.5 Hz, 2-1), 1.59 (quintet, J=7.6 Hz, 2H), 1.80-1.87 (m, 3H), 1.91-1.97 (m, 1H), 2.61 (t, J=7.7 Hz, 2H), 3.42-3.47 (m, 1H), 3.48-3.53 (m, 3H), 3.94-3.98 (m, 1H), 5.49 (s, 2H), 5.83 (s, 2H), 6.92 (d, J=7.9 Hz, 2H), 7.03 (d, J=8.0 Hz, 2H), 7.46-7.53 (m, 2H), 7.61 (t, J=7.6 Hz, 1H), 7.67 (d, J=7.7 Hz, 1H); LC-MS (M+H) found 610.1.

Example 2

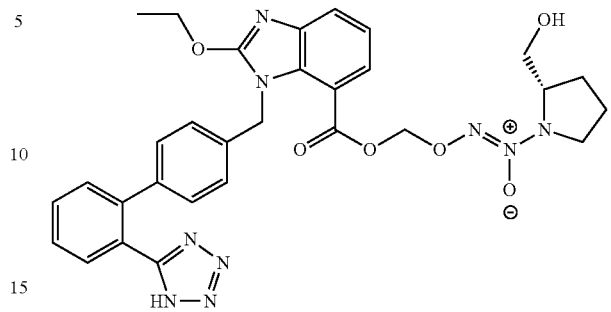

O$^2$-({[(2-ethoxy-1-{[2'-(1H-tetrazol-5-yl)biphenyl-4-yl]methyl}-1H-benzimidazol-7-yl)carbonyl]oxy}methyl)1-[2S-(hydroxymethyl)pyrrolidin-1-yl]diazen-1-ium-1,2-diolate The title compound was prepared by following the procedure for example 1, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{([2'-(1-trityl-1H-tetrazol-5-yl)biphenyl-4-yl]methyl}-1H-benzimidazole-7-carboxylic acid. NMR (500 MHz, CD$_3$CN) δ 1.42 (t, J=7.1 Hz, 3H), 1.75-1.84 (m, 3H), 1.87-1.95 (m, 1H), 3.39-3.45 (m, 1H), 3.45-3.52 (m, 3H), 3.92-3.96 (m, 1H), 4.58 (q, J=7.1 Hz, 2H), 5.52 (s, 2H), 5.80 (d, J=7.5 Hz, 1H), 5.84 (d, J=7.5 Hz, 1H), 6.91 (d, J=8.0 Hz, 2H), 6.96 (d, J=8.0 Hz, 2H), 7.17 (t, J=7.9 Hz, 1H), 7.43 (d, J=7.7 Hz, 1H), 7.51 (t, J=7.6 Hz, 1H), 7.55 (d, J=7.9 Hz, 1H), 7.60 (dt, J=1.4, 7.7 Hz, 1H), 7.63 (d, J=7.9 Hz, 1H), 7.68 (d, J=7.7 Hz, 1H); LC-MS (M+H) found 614.1.

Example 3

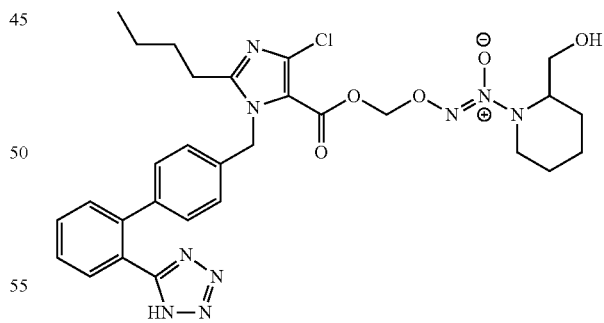

O$^2$-({[(2-butyl-4-chloro-1-{[2'-(1H-tetrazol-5-yl)biphenyl-4-yl]methyl}-1H-imidazol-5-yl)carbonyl]oxy}methyl)1-[2-(hydroxymethyl)piperidin-1-yl]diazen-1-ium-1,2-diolate The title compound was prepared by following the procedure for example 1, except that the reagent sodium 1-[2S-(hydroxymethyl)pyrrolidin-1-yl]diazen-1-ium-1,2-diolate was replaced by sodium 1-[2-(hydroxymethyl)piperidin-1-yl]diazen-1-ium-1,2-diolate. ¹H NMR (500 MHz, CDCl₃) δ 0.89 (t, J=7.4 Hz, 3H), 1.23-1.32 (m, 1H), 1.36 (sextet, J=7.5 Hz, 2H), 1.59-1.67 (m, 4H), 1.62-1.78 (m, 1H), 1.70 (quintet, J=7.8 Hz, 2H), 2.66 (t, J=7.8 Hz, 2H), 3.18-3.23 (m, 3H), 3.39 (dd, J=3.6, 12.4 Hz, 1H), 3.46 (dd, J=3.6, 12.4 Hz, 1H), 5.42 (d, J=16.6 Hz, 1H), 5.46 (d, J=16.7 Hz, 1H), 5.94 (d, J=7.2 Hz, 1H), 5.98 (d, J=7.2 Hz, 1H), 6.86 (d, J=7.9 Hz, 2H), 7.06 (d, J=7.9 Hz, 2H), 7.43 (d, J=7.7 Hz, 1H), 7.51 (t, J=7.6 Hz, 1H), 7.58 (t, J=7.6 Hz, 1H), 7.93 (d, J=7.7 Hz, 1H); LC-MS (M+H) found 624.4.

Example 4

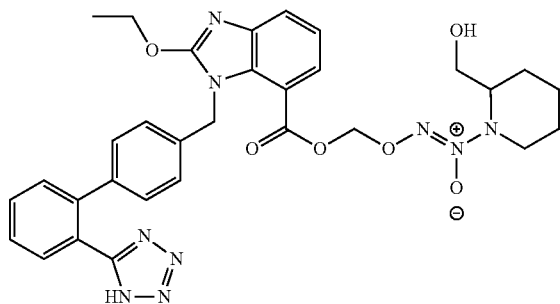

$O^2$-({[(2-ethoxy-1-{[2'-(1H-tetrazol-5-yl)biphenyl-4-yl]methyl}-1H-benzimidazol-7-yl)carbonyl]oxy}methyl)1-[2-(hydroxymethyl)piperidin-1-yl]diazen-1-ium-1,2-diolate The title compound was prepared by following the procedure for example 2, except that the reagent sodium 1-[2S-(hydroxymethyl)pyrrolidin-1-yl]diazen-1-ium-1,2-diolate was replaced by sodium 1-[2-(hydroxymethyl)piperidin-1-yl]diazen-1-ium-1,2-diolate. ¹H NMR (500 MHz, CDCl₃) δ 1.24-1.36 (m, 1H), 1.45 (t, J=7.1 Hz, 3H), 1.55-1.69 (m, 4H), 1.70-1.78 (m, 1H), 3.14-3.23 (m, 3H), 3.40 (dd, J=3.3, 12.3 Hz, 1H), 3.43-3.50 (m, 1H), 4.60 (q, J=7.1 Hz, 2H), 5.57 (d, J=16.4 Hz, 1H), 5.61 (d, J=16.8 Hz, 1H), 5.82-5.97 (m, 2H), 6.87-6.94 (m, 2H), 6.95-7.04 (m, 2H), 7.19 (t, J=7.9 Hz, 1H), 7.41 (d, J=7.7 Hz, 1H), 7.49 (t, J=7.6 Hz, 1H), 7.57 (t, J=7.6 Hz, 1H), 7.66 (d, J=8.1 Hz, 1H), 7.71 (d, J=7.9 Hz, 1H), 7.80-7.92 (m, 1H); LC-MS (M+H) found 628.5.

Example 5

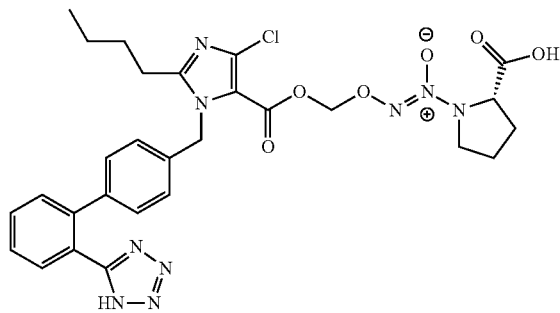

$O^2$-({[(2-butyl-4-chloro-1-{[2'-(1H-tetrazol-5-yl)biphenyl-4-yl]methyl}-1H-imidazol-5-yl)carbonyl]oxy}methyl)1-[2S-(carboxylato)pyrrolidin-1-yl]diazen-1-ium-1,2-diolate To a dichloromethane (12 mL)/water (1 mL) solution of $O^2$-({[(2-butyl-4-chloro-1-{[2'-(1-trityl-1H-tetrazol-5-yl)biphenyl-4-yl]methyl}-1H-imidazol-5-yl)carbonyl]oxy}methyl)1-[2S-(hydroxymethyl)pyrrolidin-1-yl]diazen-1-ium-1,2-diolate (prepared by following step D in example 1, 294 mg, 0.345 mmol) at 0° C. was added 1.0 M aqueous solution of sodium bromide (180 μL, 0.180 mmol), 1.0 M aqueous solution of tetrabutylammonium bromide (345 μL, 0.345 mmol), a 10% aqueous solution of sodium bicarbonate (800 μL, 1.04 mmol), and 2,2,6,6-tetramethylpiperidin-1-oxyl (24.4 mg, 0.156 mmol). The resultant mixture was charged with a 5% aqueous solution of sodium hypochlorite (1.30 mL, 1.05 mmol) and stirred for 3 hours as it was slowly warmed to room temperature. The solution was neutralized with 1 N hydrochloric acid until pH 6-7. After neutralization, tert-butyl alcohol (3 mL), sodium chlorite (330 mg, 3.65 mmol) and sodium phosphate monobasic (250 mg) in water (1.2 mL), and a 2.0 M tetrahydrofuran solution of 2-methyl-but-2-ene (1.5 mL, 3.0 mmol) were added to the reaction mixture. After 3 hours, the reaction mixture was concentrated in vacuo, redissolved in methanol (10 mL), and heated at 70° C. for 6 hours. The reaction mixture was cooled to room temperature and concentrated in vacuo. Purification of the crude product by reversed-phase mass-directed high-performance liquid chromatography afforded the title compound as a white solid. ¹H NMR (500 MHz, CDCl₃) δ 0.92 (t, J=7.3 Hz, 3H), 1.41 (sextet, J=7.5 Hz, 2H), 1.71 (quintet, J=7.6 Hz, 2H), 1.96-2.07 (m, 2H), 2.16-2.23 (m, 1H), 2.34 (qd, J=8.7, 13.2 Hz, 1H), 2.86 (t, J=7.8 Hz, 2H), 3.55 (dt, J=7.5, 8.9 Hz, 1H), 3.73 (ddd, J=5.1, 8.0, 10.1 Hz, 1H), 4.50 (dd, J=3.9, 8.9 Hz, 1H), 5.44 (d, J=16.5 Hz, 1H), 5.48 (d, J=16.5 Hz, 1H), 5.79 (d, J=7.0 Hz, 1H), 5.89 (d, J=7.0 Hz, 1H), 6.87 (d, J=8.0 Hz, 2H), 7.06 (d, J=8.0 Hz, 2H), 7.48 (dd, J=1.2, 7.7 Hz, 1H), 7.54 (dt, J=1.3, 7.6 Hz, 1H), 7.63 (dt, J=1.4, 7.6 Hz, 1H), 7.83 (dd, J=1.3, 7.7 Hz, 1H); LC-MS (M+H) found 624.4.

Example 6

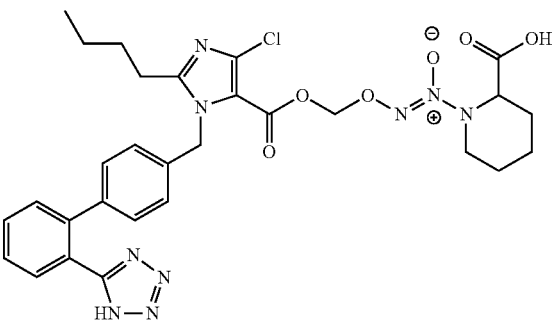

$O^2$-({[(2-butyl-4-chloro-1-{[2'-(1H-tetrazol-5-yl)biphenyl-4-yl]methyl}-1H-imidazol-5-yl)carbonyl]oxy}methyl)1-[2-(carboxylato)piperidin-1-yl]diazen-1-ium-1,2-diolate The title compound was prepared by following the procedure for example 5, except that the reagent $O^2$-({[(2-butyl-4- chloro-1-{[2'-(1-trityl-1H-tetrazol-5-yl)biphenyl-4-yl]methyl}-1H-imidazol-5-yl)carbonyl]oxy}methyl)1-[2S-(hydroxymethyl)pyrrolidin-1-yl]diazen-1-ium-1,2-diolate was replaced by O²-({[(2-butyl-4-chloro-1-{[2'-(1-trityl-1H-tetrazol-5-yl)biphenyl-4-yl]methyl}-1H-imidazol-5-yl)carbonyl]oxy}methyl)1-[2-(hydroxymethyl)piperidin-1-yl]diazen-1-ium-1,2-diolate. ¹H NMR (500 MHz, CDCl₃) δ 0.89 (t, J=7.3 Hz, 3H), 1.28-1.33 (m, 1H), 1.37 (sextet, J=7.4 Hz, 2H), 1.57-1.64 (m, 2H), 1.67 (quintet, J=7.7 Hz, 2H), 1.78-1.93 (m, 2H), 2.17-2.26 (m, 1H), 2.75 (t, J=7.8 Hz, 2H), 3.45 (dt, J=3.4, 11.2 Hz, 1H), 3.80 (td, J=4.3, 11.6 Hz, 1H), 4.73 (t, J=4.6 Hz, 1H), 5.44 (s, 2H), 5.84 (d, J=7.1 Hz, 1H), 5.87 (d, J=7.1 Hz, 1H), 6.83 (d, J=7.9 Hz, 2H), 7.04 (d, J=8.0 Hz, 2H), 7.45 (d, J=7.7 Hz, 1H), 7.52 (dt, J=1.3, 7.6 Hz, 1H), 7.60 (dt, J=1.4, 7.6 Hz, 1H), 7.84 (d, J=7.7 Hz, 1H); LC-MS (M+H) found 638.5.

Example 7

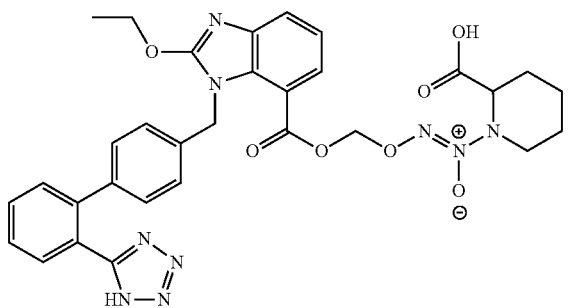

O²-({[(2-ethoxy-1-{[2'-(1H-tetrazol-5-yl)biphenyl-4-yl]methyl}-1H-benzimidazol-7-yl)carbonyl]oxy}methyl)1-[2-(carboxylato)piperidin-1-yl]diazen-1-ium-1,2-diolate Step A: O²-({[(2-ethoxy-1-[2'-(1-trityl-1H-tetrazol-5-yl)biphenyl-4-yl]methyl-1H-benzimidazol-7-yl)carbonyl]oxy}methyl)1-[2-(hydroxymethyl)piperidin-1-yl]diazen-1-ium-1,2-diolate The title compound was prepared by following step D in example 1, except that 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid, and O²-(chloromethyl)1-{2S-[(trichloroacetoxy)methyl]pyrrolidin-1-yl}diazen-1-ium-1,2-diolate was replaced by O²-(chloromethyl)1-{2-[(trichloroacetoxy)methyl]piperidin-1-yl}diazen-1-ium-1,2-diolate.

Step B: O²-({[(2-ethoxy-1-{[2'-(1H-tetrazol-5-yl)biphenyl-4-yl]methyl}-1H-benzimidazol-7-yl)carbonyl]oxy}methyl)1-[2-(carboxylato)piperidin-1-yl]diazen-1-ium-1,2-diolate To an acetonitrile (3 mL)/water (3 mL)/ethyl acetate (3 mL) solution of O²-({[(2-ethoxy-1-{[2'-(1-trityl-1H-tetrazol-5-yl)biphenyl-4-yl]methyl}-1H-benzimidazol-7-yl)carbonyl]oxy}methyl)1-[2-(hydroxymethyl)piperidin-1-yl]diazen-1-ium-1,2-diolate (1577 mg, 0.663 mmol) and sodium periodate (1430 mg, 6.67 mmol) was added ruthenium(IV) oxide (90.1 mg, 0.677 mmol). After 12 hours of stirring, the reaction mixture was filtered through diatomaceous earth, washed with ethyl acetate, and concentrated in vacuo. The residue was redissolved in methanol (5 mL) and heated at 70° C. for 3 hours. The reaction mixture was cooled to room temperature and concentrated in vacuo. Purification of the crude product by reversed-phase mass-directed high-performance liquid chromatography, using ammonium formate as a buffer, afforded the title compound as a white solid. ¹H NMR (500 MHz, CD₃CN) δ 1.25-1.35 (m, 1H), 1.42 (t, J=7.1 Hz, 3H), 1.45-1.60 (m, 2H), 1.67-1.86 (m, 2H), 1.97-2.05 (m, 1H), 3.45 (dt, J=3.7, 10.7 Hz, 1H), 3.66 (td, J=4.8, 11.3 Hz, 1H), 4.53 (t, J=5.1 Hz, 1H), 4.60 (q, J=7.1 Hz, 2H), 5.50 (d, J=16.2 Hz, 1H), 5.56 (d, J=16.2 Hz, 1H), 5.83 (d, J=7.5 Hz, 1H), 5.86 (d, J=7.5 Hz, 1H), 6.92 (d, J=8.1 Hz, 2H), 6.99 (d, J=8.2 Hz, 2H), 7.19 (t, J=7.9 Hz, 1H), 7.42 (d, J=7.8 Hz, 1H), 7.49 (dt, J=1.3, 7.6 Hz, 1H), 7.55-7.60 (m, 2H), 7.62 (d, J=7.7 Hz, 1H), 7.67 (dd, J=1.2, 7.9 Hz, 1H); LC-MS (M+H) found 642.6.

Additional exemplary compounds are shown below:

Example 8

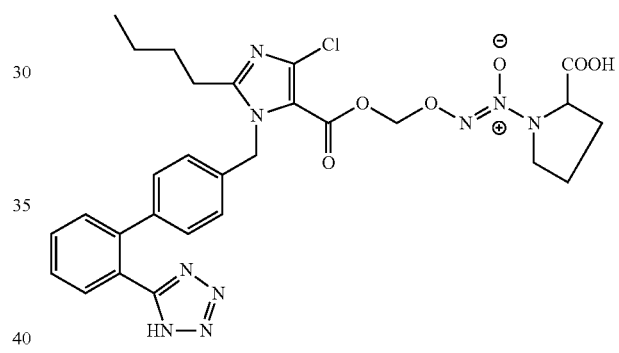

Example 9

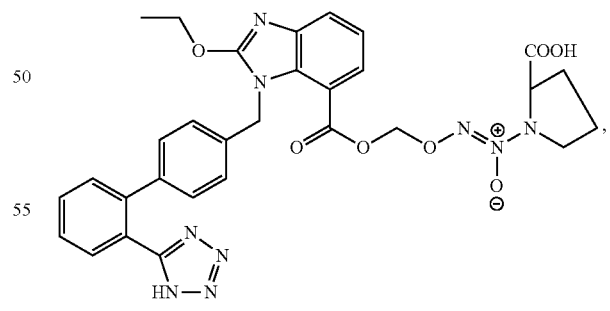

Example 10

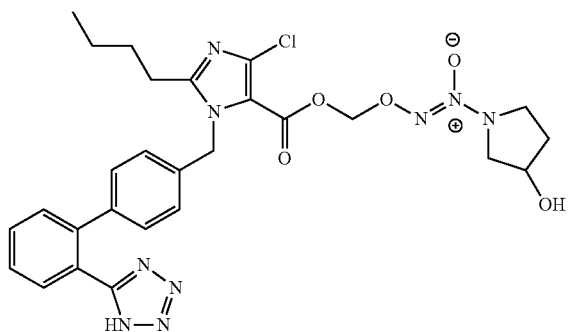

Example 11

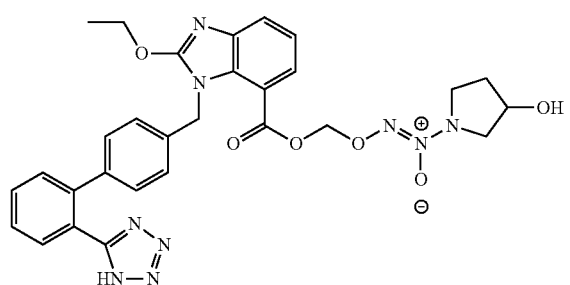

Example 12

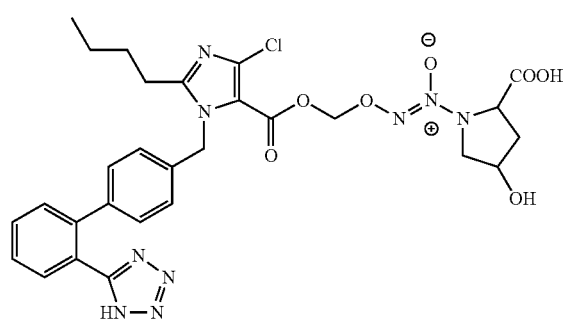

Example 13

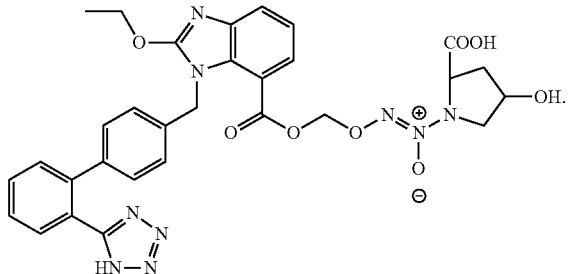

Vessel Relaxation

The ability of the compounds to induce vasorelaxation was tested in vitro in isolated rabbit thoracic aorta preparations (Wanstall J. C. et al., Br. J. Pharmacol., 134:463-472, 2001). Male New Zealand rabbits were anaesthetized with thiopental-Na (50 mg/kg, iv), sacrificed by exsanguinations and then the thorax was opened and the aorta dissected. Aortic ring preparations (4 mm in length) were set up in physiological salt solution (PSS) at 37° C. in small organ chambers (5 ml). The composition of PSS was (mM): NaCl 130, NaHCO$_3$ 14.9, KH$_2$PO$_4$ 1.2, MgSO$_4$ 1.2, HEPES 10, CaCl$_2$, ascorbic acid 170 and glucose 1.1 (95% O$_2$/5% CO$_2$; pH 7.4). Each ring was mounted under 2 g passive tension. Isometric tension was recorded with a Grass transducer (Grass FT03) attached to a BIOPAC MP150 System. Preparations were allowed to equilibrate for 1 h, and then contracted submaximally with noradrenaline (NA, 1 µM) and, when the contraction was stable, acetylcholine (ACh, 10 µM) was added. A relaxant response to ACh indicated the presence of a functional endothelium. Vessels that were unable to contract NA or showed no relaxation to ACh were discarded. When a stable precontraction was reached, a cumulative concentration-response curve to either of the vasorelaxant agents was obtained in the presence of a functional endothelium. Each arterial ring was exposed to only one combination of inhibitor and vasorelaxant. Moreover, the effect of the soluble guanylyl cyclase inhibitor ODQ (1-H-(1,2,4)-oxadiazol(4,3-a)quinoxalin-1-one) on vasorelaxation elicited by the compounds was examined preincubating the aortic rings with ODQ (10 µM) for 20 min.

Examples 3 and 5 were evaluated for vessel relaxation. In vitro, tissue-based measure of vessel relaxation, determined in rabbit aortic slices, demonstrated vessel relaxation according to the indicated EC$_{50}$ (molar concentration of compound which produces 50% of the maximum possible response for that compound—Data Table 1).

DATA TABLE 1

| | EC$_{50}$ in vessel relaxation assay |
|---|---|
| Example 3 | 5.3 µM |
| Example 5 | 18.7 µM |

What is claimed is:
1. A compound having the general formula:

R—Y
|
[Y]$_{0-1}$ wherein R is

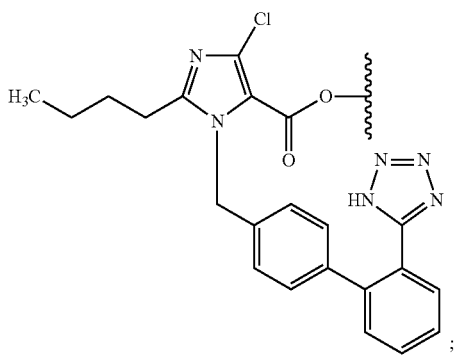

Y is —(CR$^1$R$^{20}$)$_{1-7}$R$^5$, or —C(O)(CR$^1$R$^{20}$)$_{1-7}$R$^5$;

R$^1$ and R$^{20}$ are independently selected from the group consisting of hydrogen or C$_{1-4}$ alkyl;

R$^5$ is —O—N=N(O)—NR$^3$R$^4$;

R$^3$ and R$^4$ together with the nitrogen atom to which they are attached, form a ring selected from the group consisting of

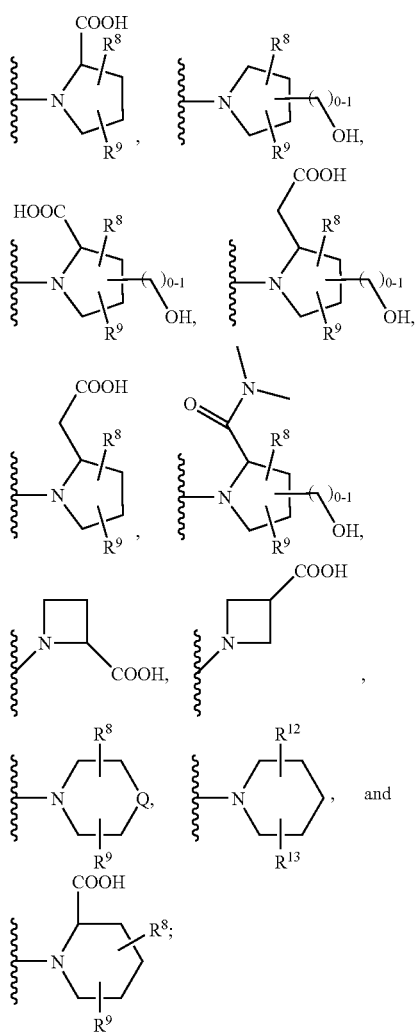

Q is selected from the group consisting of S, O and NR$^6$;

R$^6$, R$^8$ and R$^9$ are independently selected from the group consisting of hydrogen and unsubstituted or substituted C$_{1-6}$ alkyl;

R$^{12}$ and R$^{13}$ are independently selected from the group consisting of —OH, —CH$_2$OH, —CH$_2$CH$_2$OH, —COOH, and —CH$_2$COOH;

or a stereoisomer thereof, or a pharmaceutically acceptable salt thereof, or a pharmaceutically acceptable salt of the stereoisomer thereof.

2. A compound of claim 1, or a pharmaceutically acceptable salt thereof, wherein R$^1$ is H or CH$_3$.

3. A compound of claim 1, or a pharmaceutically acceptable salt thereof, wherein R$^3$ and R$^4$, together with the nitrogen atom to which they are attached, form a ring selected from the group consisting of

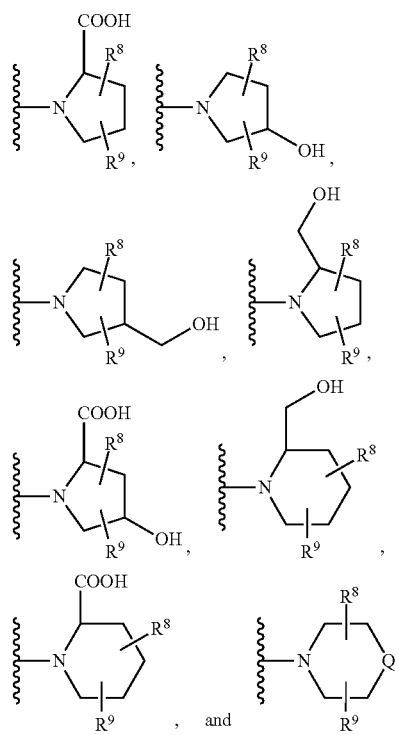

4. A compound of claim 1, or a pharmaceutically acceptable salt thereof, wherein R$^8$ and R$^9$ are hydrogen.

5. A compound of claim 1, or a pharmaceutically acceptable salt thereof, selected from the group consisting of

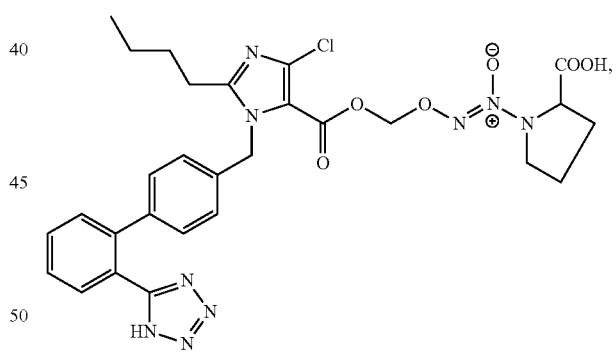

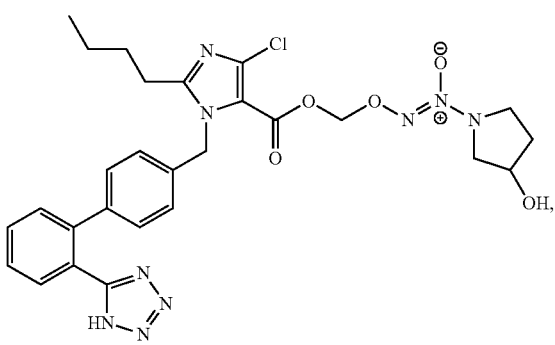

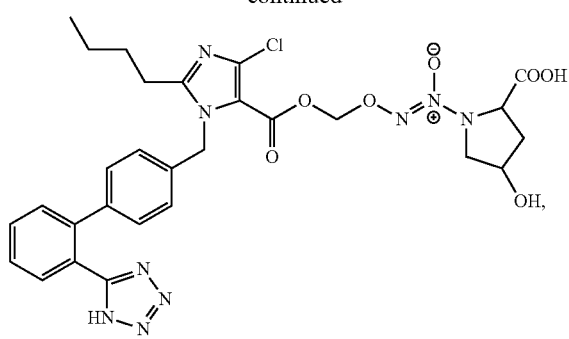

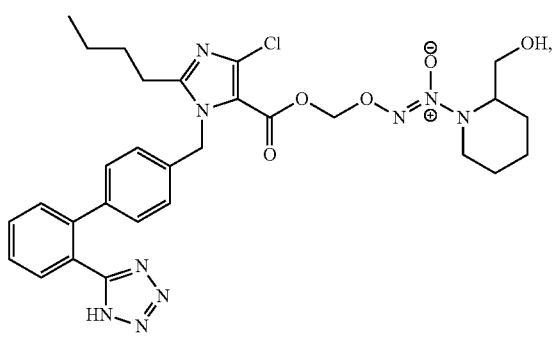

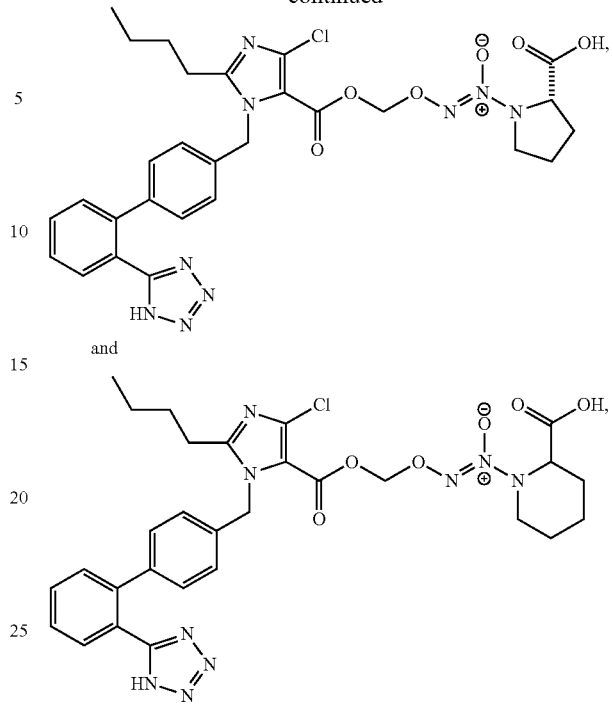

and

6. A pharmaceutical composition comprising a compound of claim 1 and a pharmaceutically acceptable carrier.

7. A pharmaceutical composition comprising a compound of claim 1, a diuretic, and a pharmaceutically acceptable carrier.

8. A method for treating hypertension in a patient which comprises administering to the patient a therapeutically effective amount of the composition of claim 6.

9. A pharmaceutical composition comprising a compound of claim 5 and a pharmaceutically acceptable carrier.

10. A pharmaceutical composition comprising a compound of claim 5, a diuretic, and a pharmaceutically acceptable carrier.

11. A method for treating hypertension in a patient which comprises administering to the patient a therapeutically effective amount of the composition of claim 10.

* * * * *